United States Patent
Zhu et al.

(10) Patent No.: US 7,012,158 B2
(45) Date of Patent: *Mar. 14, 2006

(54) PROCESSES FOR THE PRODUCTION OF α-DIFLUOROMETHYL ORNITHINE (DFMO)

(75) Inventors: Jingyang Zhu, Jamesville, NY (US); Scott T. Chadwick, Tully, NY (US); Benjamin A. Price, DeWitt, NY (US); Shannon X. Zhao, East Syracuse, NY (US); Carrie A. Costello, Syracuse, NY (US); Purushotham Vemishetti, East Syracuse, NY (US)

(73) Assignee: Skinmedica, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/788,728

(22) Filed: Feb. 26, 2004

(65) Prior Publication Data

US 2004/0171876 A1    Sep. 2, 2004

Related U.S. Application Data

(63) Continuation of application No. 10/224,890, filed on Aug. 19, 2002, now Pat. No. 6,730,809.

(60) Provisional application No. 60/315,832, filed on Aug. 29, 2001.

(51) Int. Cl.
*C07C 258/00* (2006.01)
*C07C 229/00* (2006.01)

(52) U.S. Cl. ............................. 562/561; 558/441

(58) Field of Classification Search ............... 562/561; 558/441
See application file for complete search history.

(56) References Cited

U.S. PATENT DOCUMENTS 6,730,809 B1 *   5/2004   Zhu et al. ............... 562/561

OTHER PUBLICATIONS

Seki et al , Convenient synthesis of alph-difluoromethylornithine, Jun., 1993, Biscience, Biotech, and Biochem. , vol . 57, p. 1024-1025.*

P.Bey et al , Catalytic Irreversible Inhibition of mammalian Ornithine Decaaarboxylase by substrate and product analogues, 1978, J. Am. chem. soc. , 100, p. 2551-2553.*

* cited by examiner

*Primary Examiner*—Cecilia J. Tsang
*Assistant Examiner*—Taylor Victor Oh
(74) *Attorney, Agent, or Firm*—Wilson Sonsini Goodrich & Rosati

(57) ABSTRACT

Provided are processes and synthetic intermediates useful for the preparation of α-difluoromethylornithine (DFMO) having the formula

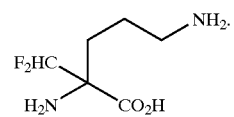

6 Claims, No Drawings

PROCESSES FOR THE PRODUCTION OF α-DIFLUOROMETHYL ORNITHINE (DFMO)

RELATED APPLICATIONS

This application is a continuation of U.S. patent application Ser. No. 10/224,890 entitled "PROCESSES FOR THE PRODUCTION OF α-DIFLUOROMETHYL ORNITHINE (DFMO)" and filed on Aug. 19, 2002 now U.S. Pat. No. 6,730,809, which claims priority to U.S. Provisional Application No. 60/315,832 entitled "PROCESSES FOR THE PRODUCTION OF α-DIFLUOROMETHYL ORNITHINE (DFMO)" filed on Aug. 29, 2001. The subject matter of the aforementioned applications are hereby incorporated by reference in their entirety.

FIELD OF THE INVENTION

The present invention relates to novel processes and synthetic intermediates for the preparation of α-difluoromethyl ornithine.

Eflornithine or α-difluoromethylornithine (DFMO) has recently been approved in the United States in a topical cream for removing unwanted facial hair. Efficient, scaleable syntheses of DFMO are therefor useful to provide manufacturing processes.

A preparation of DFMO have been described previously in U.S. Pat. No. 4,309,442 from ornithine. The relatively high cost of the starting material, ornithine, and the use of less desirable reagents including flammable reagents, however, makes the route less attractive for commercial manufacture.

An alternative preparation of DFMO was described in Swiss patent CH 672 124 from starting materials including malonic acid esters and acrylonitrile. The process is burdened by the use of a Hoffman type reaction which is a potential run-away reaction.

From a manufacturing standpoint it would be advantageous to have a process for the synthesis of DFMO that utilizes readily available and inexpensive starting materials. Processes for DFMO that avoid potentially explosive reaction conditions are also highly desirable. In addition, processes for DFMO production that would avoid the use of halogenated solvents, which require costly waste disposal protocols and emissions monitoring are also preferable.

SUMMARY OF THE INVENTION

In one embodiment, the invention relates to processes for the preparation of DFMO, having the formula

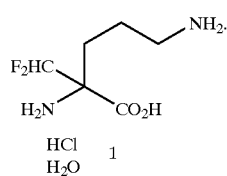

The processes include the step of selectively reducing a nitrile moiety of a compound of the formula

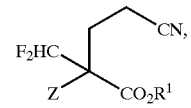

wherein $R^1$ is linear or branched $C_1$ to $C_4$ alkyl and Z is (i) —$NH_2$ or (ii) a protected amino moiety selected from the group consisting of

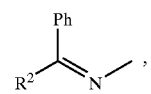

wherein $R^2$ is hydrogen, linear or branched $C_1$ to $C_4$ alkyl or aryl, and

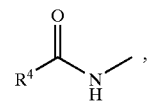

wherein $R^4$ is linear or branched $C_1$ to $C_4$ alkyl, alkoxy or aryl.

In another or the same step, the

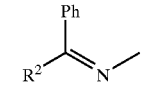

moiety, if present, is hydrolyzed, producing as a result of the reduction step, or the reduction followed by hydrolysis steps, a compound of one of the following formulas

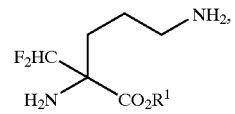

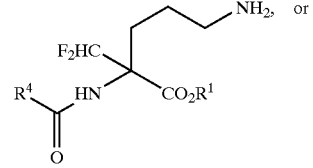

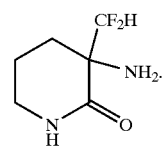

In another step the ester and amide (including the lactam) moieties of formulas 7, 9, or 10 are hydrolyzed to give the compound of formula 1.

In another aspect, the invention relates to intermediates useful in the preparation of DFMO. The intermediates include compounds of the formula

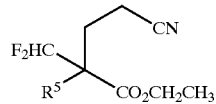

wherein $R^5$ is: (a)

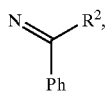

wherein $R^2$ is hydrogen, linear or branched $C_1$ to $C_4$ alkyl or aryl; (b) $NH_2$; or (c)

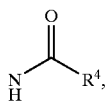

wherein $R^4$ is linear or branched $C_1$ to $C_4$ alkyl, alkoxy or aryl. Preferred intermediates include: ethyl 2-benzylidene-amino-2-difluoromethyl-4-cyanobutanoate, ethyl 2-(diphenylmethylene)amino-2-difluoromethyl-4-cyanobutanoate, ethyl 2-amino-2-difluoromethyl-4-cyanobutanoate, or ethyl 2-acetylamino-2-difluoromethyl-4-cyanobutanoate, or salts thereof.

DETAILED DESCRIPTION OF THE INVENTION

In accordance with the present invention, novel processes and intermediates for the preparation of difluoromethyl ornithine (DFMO or the compound of formula 1) are provided. The processes of the invention have been developed from readily available and inexpensive starting materials. Furthermore, the processes provide high yields of DFMO, simplify isolation and purification steps, and minimize the use of halogenated solvents.

In one embodiment of the invention an alkyl glycine ester of the formula 2 serves as a convenient starting material for a short synthesis of an alkyl 2-difluoromethyl-4-cyanobutanoate intermediate (compound of the formula 5) wherein $R^1$ is $C_1$ to $C_4$ linear or branched alkyl and $R^2$ is hydrogen, $C_1$ to $C_4$ linear or branched alkyl, or aryl. Compound of the formula 5 can then be converted by a number of processes to DFMO.

Scheme 1

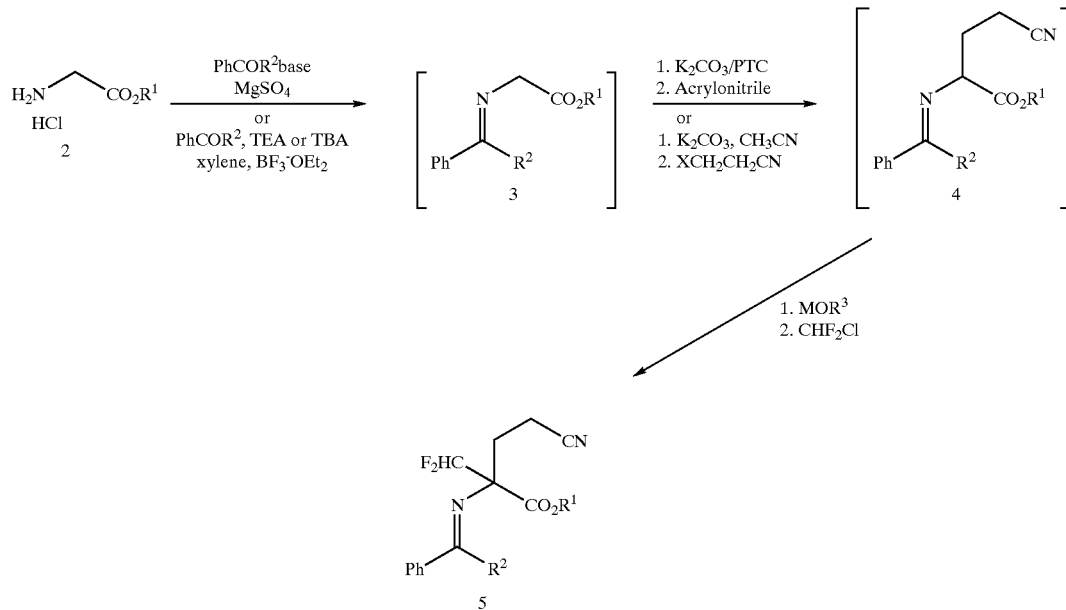

The compound of formula 3 can be obtained from the glycine ester of the formula $H_2NCH_2CO_2R^1$, (formula 2) wherein $R^1$ is $C_1$ to $C_4$ alkyl. Preferably the alkyl group is methyl, ethyl, or t-butyl. Glycine ethyl ester, for example, is readily available from a number of commercial vendors as its hydrochloride salt. The compound of the formula 3 can be formed by treatment of the glycine ester of the formula 1 with an aryl aldehyde or ketone of the formula PhC(O)R$^2$, wherein R$^2$ is hydrogen, C$_1$ to C$_4$ alkyl or aryl (Scheme 1). A dehydrating agent such as magnesium sulfate or sodium sulfate can optionally be used to remove the water generated in the reaction. If the glycine ester of the formula 2 is provided as an acid addition salt, a tertiary amine base, e.g., triethylamine (TEA), tributylamine (TBA) or N,N-diisopropylethylamine, can be included in the reaction mixture to generate the neutral form of the ester.

While conventional methods for the preparation of Schiff's base derivatives of glycine alkyl ester utilize halogenated reaction solvents such as dichloromethane, applicants have found that the reaction for the preparation of aldimine type intermediates (R$^2$=H), can be advantageously carried out in acetonitrile at temperatures of about 10 to 35° C., preferably at about 20 to 25° C. The use of acetonitrile as a reaction solvent simplifies reaction work-up procedures and processing. The magnesium sulfate and tertiary amine base-acid addition salt (if used) can be simply removed by, for example, filtration, and the filtrate used directly in the next synthetic step, where acetonitrile also serves as the reaction solvent.

These reaction conditions can provide high yields and conversions, preferably >98% for both yield and conversion, of compound of the formula 3.

In embodiments of the process where the amino group is protected as a ketone imine (i.e., R$^2$=C$_1$ to C$_4$ alkyl or aryl) the condensation reaction can also be accomplished using an aprotic solvent, e.g., xylene or toluene (preferably toluene), and catalytic amount of a Lewis acid, e.g., boron trifluoride etherate, triphenyl boron, zinc chloride, aluminum chloride, and the like. The condensation reaction can include the use of a Dean Stark trap and/or the use of other such dehydrating techniques known to those of ordinary skill to hasten the reaction rate by removing the formed water effectively.

The alkyl 4-cyanobutanoate of the formula 4 is, in one embodiment, obtained from the compound of the formula 3 by a Michael reaction. For example, compound of the formula 3 is treated with acrylonitrile, a base such as potassium carbonate and a phase transfer catalyst (PTC), such as triethylbenzylammonium chloride, tetrabutylammonium chloride, tetraethylammonium chloride, or trimethylbenzylammonium chloride at temperatures of from about 10 to about 45° C., preferably from about 20 to 35° C. Methods for the phase transfer catalyzed Michael addition of α-amino acids wherein the α-amino groups are protected as benzaldimines can be found in Yaozhong et al., *Tetrahedron* 1988, 44, 5343–5353.

The compound of formula 4 is then alkylated using a strong base and a halodifluoromethane alkylating reagent to form the compound of formula 5. Suitable strong bases include those that are effective in deprotonating the compound of formula 4 at the position α to the carboxylate. Examples of strong bases include alkali metal alkoxides of the formula MOR$^3$ wherein M is Na, Li or K and R$^3$ is C$_1$ to C$_4$ linear or branched alkyl; alkali metal hydrides, or alkali metal amide (e.g., sodium amide, sodium bistrimethylsilylamides). Preferably the alkoxide base is either a sodium or potassium alkoxide, more preferably a sodium alkoxide, such as sodium ethoxide or sodium t-butoxide. Preferably, a slight molar excess of base is used in the reaction such as from about 1.6 to 2.0 equivalents.

The alkylation reaction is carried out, for example, by deprotonation at a temperature of from about −35 to about 25° C. Once the α-anion has been generated, the alkylating reagent is introduced and the temperature of the reaction can be, for example, from about −5 to about 20° C. (for R$^2$=aryl). Useful halodifluoromethane alkylating reagents include difluoroiodomethane, chlorodifluoromethane, or bromodifluoromethane. Preferably the halodifluoromethyl alkylating reagent is chlorodifluoromethane. Typically an excess of the halodifluoromethyl alkylating reagent is used in the reaction such as from about 1.05 to about 2.0 molar equivalents. In instances where the alkylation reaction is run in a pressure vessel, smaller amounts of the halodifluoromethyl alkylating agent are used.

The alkylation reaction is carried out in suitable aprotic solvents such as dimethylformamide, acetonitrile, N-methylpyrrolidone, dimethylsulfoxide, or an ether such as tetrahydrofuran, 2-methyltetrahydrofuran, methyl t-butyl ether, diethyl ether, dioxane, or mixtures thereof. Preferably the solvent used in this alkylation reaction is an ether, preferably tetrahydrofuran or tetrahydrofuran/acetonitrile.

In Process A (Scheme 2, Route I) for the synthesis of DFMO, the synthetic steps include: hydrolysis of the Schiff's base protecting group, reduction of the nitrile moiety and hydrolysis of the alkyl ester moiety. The Schiff's base protecting group of the compound of the formula 5 is hydrolyzed by treatment with an aqueous acid using conditions well known in the art, to provide the compound of formula 6. Suitable acids include mineral acids, toluenesulfonic acid, methanesulfonic acid, trifluoroacetic acid, and the like. The reaction is conveniently carried out in a mixture of the aqueous acid and an organic solvent. For example, a mixture of methyl t-butyl ether and 4 N HCl is stirred at ambient temperature to effect hydrolysis of the Schiff's base. After the reaction mixture is made basic with hydroxide solution, the compound of formula 6 isolated in neutral form and used directly without further purification in the next synthetic step.

Scheme 2

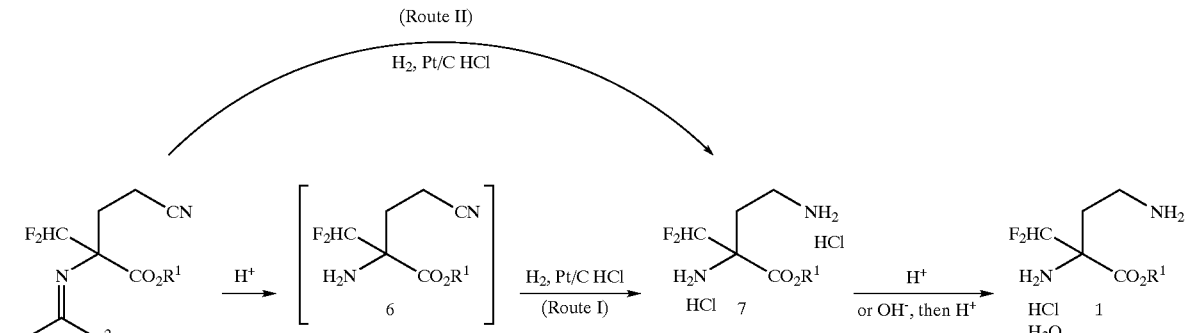

The compound of the formula 6 is then converted to the diamino compound of formula 7 by reduction of the nitrile moiety. Any reduction procedure effective to selectively reduce the nitrile moiety to the amine with minimal competing ester reduction can be used. For example, heterogeneous transition metal catalysts are effective catalysts for the hydrogenation of the nitrile moiety. Typically an acid such as hydrochloric acid is added to the reaction mixture. The transition metal catalysts include, for example, palladium on carbon, platinum on carbon, and platinum oxide. Preferably the catalyst used in the reduction is 5–10% platinum on carbon.

The amount of hydrochloric acid typically used in the reaction is 1 to 5 equivalents, more preferably 3 to 4 equivalents. The reaction solvent for the hydrogenation can be an alcohol, preferably ethanol or an ether, preferably t-butyl methyl ether. The reaction is carried out in a suitable corrosive resistant reaction vessel such as a Hastelloy bomb vessel with hydrogen at a pressure of, for example, from about 80 to about 120 psi. The hydrogenation is typically run at temperatures from about 25 to about 40° C., preferably about 25 to 30° C.

DFMO can be obtained by hydrolysis of the alkyl ester moiety of the diamino compound of the formula 7. In one embodiment, the alkyl ester moiety can be hydrolyzed using aqueous basic conditions well known to those of ordinary skill in the art. Alternatively, the alkyl ester moiety can be hydrolyzed using acidic conditions. Suitable acids for the hydrolysis reaction include mineral acids or toluene sulfonic acid. Preferably the hydrolysis is effected using an excess of mineral acid, for example 12 N HCl at reflux. In the instance where $R^1$ is a t-butyl ester, the t-butyl ester can also be hydrolyzed by milder acidic hydrolysis methods well known in the art, such as treatment with formic acid or trifluoroacetic acid.

DFMO can be conveniently isolated as its monohydrochloride monohydrate salt. For example, a solution of from about 9 to about 13% by weight DFMO in about a 1 to 3–3.5 mixture of aqueous hydrochloric acid 12 N and alcohol, preferably ethanol, is provided with a pH of less than 0.5. The resulting solution can be treated with sufficient triethylamine to effect a pH of about 4 to form a slurry containing precipitated DFMO dihydrochloride. The precipitated DFMO hydrochloride monohydrate is recovered by methods well known to those of ordinary skill in the art including filtration and centrifugation. The crude DFMO recovered can be further purified by recrystallization from suitable recrystallizing solvents such as ethanol/water. Preferably the purity of the DFMO is at least 98%, more preferably at least 99% pure.

In alternative embodiments of Process A, metal hydride reagents can be used to effect the selective reduction of the nitrile moiety. These hydride reagents include $NaBH_3(O_2CCF_3)$ and other such modified borohydride and aluminum hydride reagents that selectively reduce the nitrile moiety in the presence of a carboxylic ester moiety.

In a closely related embodiment of this metal hydride process, the ester moiety of the amino compound of formula 6 is hydrolyzed before reducing the nitrile group with a metal hydride. For example the alkyl ester of the amino compound of formula 6 is saponified to give a carboxylate salt. The nitrile is then selectively reduced to the amine by treatment with $NaBH_3(O_2CCF_3)$, and other such modified borohydride and aluminum hydride reagents that selectively reduce the nitrile moiety in the presence of a carboxylic acid or acid salt.

In another embodiment of Process A (Scheme 2, Route II), the compound of formula 5 is directly hydrogenated to form the diamino compound of formula 7 using a heterogeneous transition metal catalyst, e.g., platinum on carbon, using hydrochloric acid and a solvent such as ethanol.

In Process B, the compound of the formula 6 is converted to the compound of formula 1 via the lactam compound of the formula 10 (Scheme 3). In this instance, compound of formula 6 (e.g., wherein $R^1$=ethyl) is treated with a base metal catalyst under neutral conditions to reduce the nitrile moiety to an amino moiety. Base metal catalysts effective for the nitrile reduction include nickel-, cobalt-, or copper-aluminum alloy catalysts. A preferred catalyst is a cobalt-aluminum alloy catalyst such as that sold as Raney cobalt catalyst by Engelhard Corporation. Suitable solvents for the reduction include ethanol, methyl t-butyl ether, tetrahydrofuran, isopropanol, and the like. The lactam is hydrolyzed under basic conditions such as 10 N hydroxide solution or under acidic conditions using a suitably strong acid such as 12 N HCl. Preferably the lactam is hydrolyzed under acidic conditions using a mineral acid. DFMO is conveniently isolated as its monohydrochloride monohydrate salt as described above.

Scheme 3

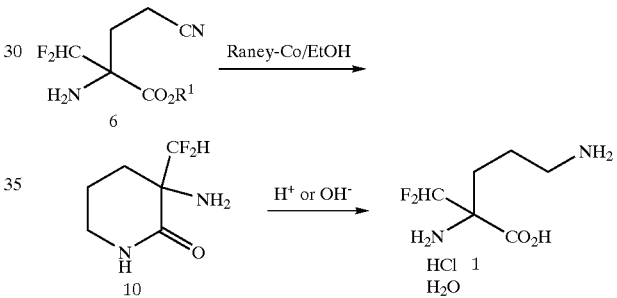

In Process C, the nitrile moiety of the compound of the formula 5 (preferably wherein $R^2$ is aryl) is reduced to an amine before the 2-amino protecting group is removed (Scheme 4). Compound of the formula 5 is treated with a base metal catalyst to reduce the nitrile moiety and provide the compound of the formula 11. Base metal catalysts that can be used for this reduction reaction include nickel-, cobalt-, or copper-aluminum alloy catalysts. Preferably the catalyst is a cobalt-aluminum alloy catalyst. Solvents useful in the reduction reaction include alcohols, e.g., ethanol and ethers, e.g., methyl t-butyl ether. The Schiff's base can be removed by acid hydrolysis, as described above for Process A, and the ester group is further removed to complete the preparation of DFMO.

Scheme 4

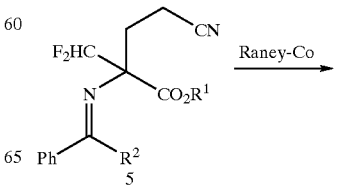

-continued

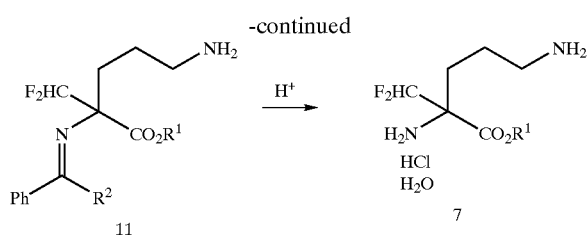

In Process D, the amino protecting group in the compound of formula 5, is switched from a Schiff's base protecting group to an amide (or carbamate) protecting group (Scheme 5). The compound of the formula 8, wherein $R^4$ is linear or branched $C_1$ to $C_4$ alkyl, alkoxy or aryl, is obtained by treating the compound of formula 5 with suitable acylating reagents. The acylating agents include anhydrides, acid chlorides, chloroformates, activated esters, e.g. N-hydroxysuccinimide esters, or other acylating agents well known to those of ordinary skill in the art. Preferably the acylating reagent is acetic anhydride so that $R^4$ is methyl in the compound of formula 8. The acylation reaction can be performed in ethers, dimethylformamide, dimethylacetamide, esters (e.g., ethyl acetate) as well as other solvents, in the presence of an organic base such as triethylamine or pyridine.

the ester and amide moieties are hydrolyzed simultaneously using acidic conditions, e.g., 12 N HCl. DFMO can be isolated and further purified as its monohydrochloride monohydrate salt as described above.

It can be recognized that the compound of formula 1 or its synthetic precursors can be resolved into its individual isomers by resolution techniques well-known to those of ordinary skill in the art. For example, the lactam of the compound of formula can be formed, i.e., the compound of formula 10, and then the acid addition salt of the lactam can be prepared with a homochiral acid such as (+) or (−) binaphthylphosphoric acid as described in U.S. Pat. No. 4,309,442. Other resolving agents, i.e., homochiral acids, well-known in the art could also be employed. Alternatively, chiral reversed phase chromatography techniques can be used to resolve the product if desired.

DFMO is typically produced by the process of the invention as a salt. The salt can be exchanged by a pharmaceutically acceptable salt as needed to provide the desired formulation.

The following examples further illustrate the present invention, but of course, should not be construed as in any way limiting its scope.

Scheme 5

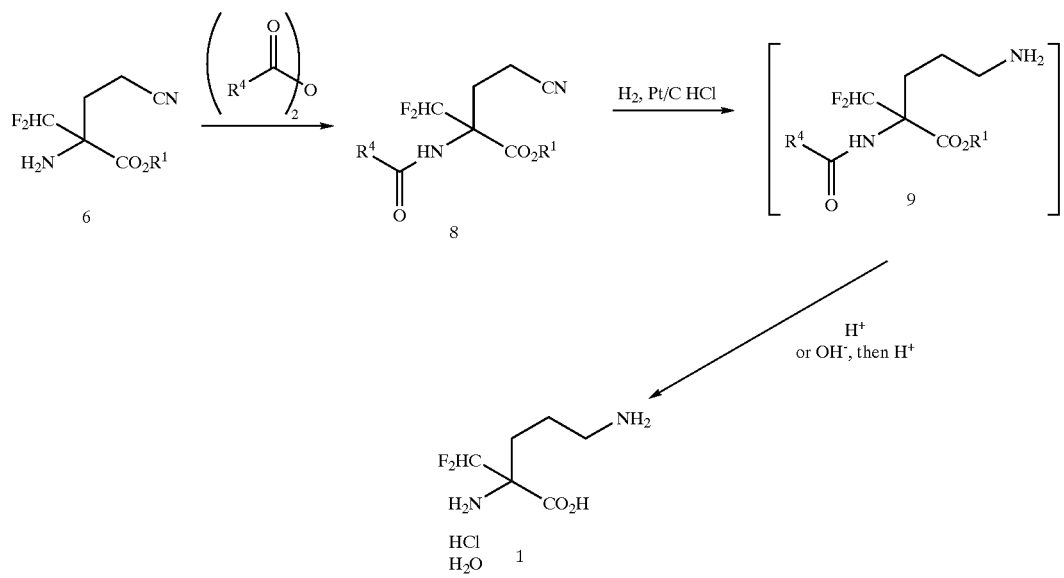

The nitrile group of the compound of formula 8 is then reduced using procedures analogous to those described above for Process A to provide the compound of formula 9. Although the compound of formula 9 can be isolated and further purified, it can be conveniently used in the next step without further purification. In the final step, the ester and amide moieties of the compound of formula 9 are hydrolyzed to provide DFMO. The hydrolysis can be accomplished by first hydrolyzing the carboxylic acid ester moiety with aqueous base followed by acid hydrolysis of the amide moiety with, for example, mineral acids. Alternatively, both

EXAMPLE 1

Preparation of Ethyl 2-Benzylideneamino-2-difluoromethyl-4-cyanobutyrate

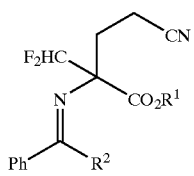

($R^1$=CH$_3$CH$_2$, $R^2$=H)

Preparation of 2-Benzylideneamino Glycine Ethyl Ester

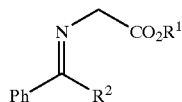
3

($R^1$=$CH_3CH_2$), $R^2$=H)

To a 2 L flask, equipped with an overhead stirrer, was added 101.1 g of glycine ethyl ester hydrochloride salt (1.05 eq), 82.1 g magnesium sulfate (1.0 eq), 0.5 L acetonitrile, 72.7 g benzaldehyde (1.0 eq), and 138.7 g triethylamine (2 eq). The reaction mixture was stirred at 20–25° C. for ~4 h. The solid was filtered off, and washed with 2×0.1 L acetonitrile. The crude product (filtrate) was ready for use in the next step.

Preparation of Ethyl 2-Benzylideneamino-4-cyanobutyrate

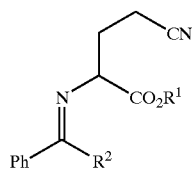
4

($R^1$=$CH_3CH_2$, $R^2$=H)

To the reaction mixture obtained above, was added 274.2 g potassium carbonate (3 eq) and 14.9 g triethylbenzylammonium chloride (0.1 eq). The reaction mixture was stirred at 20–25° C. for 1 h. Acrylonitrile (32.9 g, 0.95 eq) was subsequently added while maintaining the temperature below 35° C. (increase of temperature within 10° C.). The mixture was stirred at 20–25° C. for ~2 h. After the reaction was complete, the solid was filtered off, and washed with acetonitrile (2×0.25 L). Acetonitrile was removed under reduced pressure until ~85% solvent (by volume) was removed. The crude product 4 was ready for use in the next step.

Preparation of Ethyl 2-Benzylideneamino-2-difluoromethyl-4-cyanobutyrate

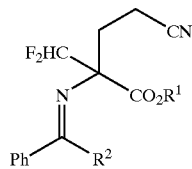
5

($R^1$=$CH_3CH_2$, $R^2$=H)

To the solution of crude ethyl 2-benzylideneamino-4-cyanobutyrate (4) obtained above, was added 0.35 L of tetrahydrofuran (THF) and 28.0 g of lithium t-butoxide (1.6 eq) at 5° C. The mixture was stirred at ~5° C. for 0.5 h, at 20–25° C. for 2 h, and then warmed to 40° C. Chlorodifluoromethane (34.2 g, 1.8 eq) was slowly bubbled into the reaction mixture, and the temperature maintained at 40–50° C. When the exotherm subsided, bubbling was continued for another ~15 min. and then stopped. The reaction mixture was stirred at 40° C. for 1–2 h. After the reaction was complete, the solvent was removed under reduced pressure. The crude product 5 was ready for use in the next step.

EXAMPLE 2

Process A (Route I)—Preparation of DFMO

Preparation of Ethyl 2-Amino-2-difluoromethyl-4-cyanobutyrate (Compound of the Formula 6)

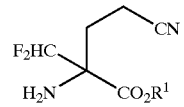
6

($R^1$=$CH_3CH_2$)

To the crude ethyl 2-benzylideneamino-2-difluoromethyl-4-cyanobutyrate (5) obtained above, was added 0.15 L 4 N HCl (2.7 eq) and 0.15 L methyl t-butyl ether (MTBE). The mixture was stirred at 20–25° C. for 1–2 h and the phases were separated. The aqueous phase was extracted with 0.2 L MTBE, and the pH adjusted to 9.5–10 with ~0.04 L 10 N NaOH at 5° C. The basic aqueous phase (pH 9.5–10) was extracted with MTBE (3×0.25 L). The pH of the aqueous phase was re-adjusted to pH 9.5–10 prior to each extraction. The organic phases were combined and concentrated under vacuum. The crude product 6 was ready for use in the next step.

Preparation of Ethyl 2,5-Diamino-2-difluoromethylpentanoate Dihydrochloride

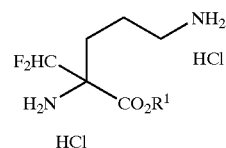
7

($R^1$=$CH_3CH_2$)

To a Hastelloy bomb vessel equipped with a stirring bar were added 10% Pt/C (0–42 g) and MTBE (10 mL). The vessel contents were purged three times with $H_2$ to 120 psi before being pressurized to 120 psi for 1 h. To the vessel were then added ethyl 2-amino-2-difluoromethyl-4-cyanobutyrate (6, 0.0189 mol, 1.0 eq), 29 mL MTBE, and 5.47 g 12 N HCl (0.0568 mol, 3.0 eq). The vessel was purged three times with hydrogen, pressurized to 120 psi, and stirred overnight for 16 h. The vessel was then de-pressurized and its contents filtered through diatomaceous earth (Celite®). The diatomaceous earth was washed with MTBE and methanol, and the filtrate was concentrated under vacuum to yield 5.53 g of crude product (103.4% weight yield, estimated ~75% pure by $^1$H NMR).

Purification of Ethyl 2,5-Diamino-2-difluoromethylpentanoate Dihydrochloride

To a 10 mL vial equipped with a stirring bar were added 1.1 g of crude ethyl 2,5-diamino-2-difluoromethylpentanoate dihydrochloride (7) and 3.3 mL isopropanol to make a 33% w/v slurry. The slurry was agitated for 30 min before being filtered. The filter cake was then washed with the mother liquor and 2×2 mL of fresh isopropanol. Drying of the cake yielded 0.86 g (89.3% recovery of product) of fine white powder that was ready to be used in the next step.

Preparation of DFMO Monohydrochloride Monohydrate (Compound of the Formula 1)

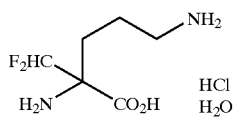

1

To a 3-neck, 50-mL round-bottomed flask equipped with a stirring bar, condenser, and thermocouple were added 3.39 g of ethyl 2,5-diamino-2-difluoromethylpentanoate dihydrochloride (7, 12 mmol, 1.0 eq) and 18.7 mL 12 N HCl (224 mmol, 18.75 eq). The flask contents were agitated and heated to reflux for 18 h before being cooled to room temperature and concentrated under reduced pressure.

Crystallization of DFMO Monohydrochloride Monohydrate

A 37% solution of 2.2 g DFMO (12 mmol, 1.0 et) in 6 mL water was diluted in EtOH (18.2) to a 9% solution having a pH of 0. 4.2 mL of triethylamine (0.030 mol, 2.52 eq) was added dropwise at room temperature to bring the pH up to 4 and to form a slurry. The slurry was further agitated for 30 min. before being filtered off and the cake was washed with EtOH. The solids were then pulled dry yielding 1.64 g (57.9% yield) of pure white powder (~97% pure). The product can be further purified by the treatment of activated carbon and recrystallization from ethanol/water.

EXAMPLE 3

Preparation of Ethyl N-(Diphenylmethylene)amino 2-Difluoromethyl-4-Cyanobutyrate

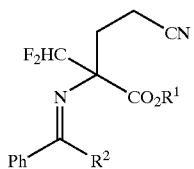

5

($R^1$=$CH_3CH_2$, $R^2$=Ph)

Preparation of N-(Diphenylmethylene)glycine Ethyl Ester

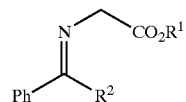

2

($R^1$=$CH_3CH_2$, $R^2$=Ph)

To a 250 mL round bottom flask, was added 5.52 g of benzophenone (1 eq), 8.46 g of glycine ethyl ester hydrochloride (1, 2 eq), 67 mL of toluene, and a trace amount of BF$_3$.Et$_2$O. The slurry was heated to reflux (112~113° C.). Tributylamine (11.2 g) was then added dropwise over 120 min. The reaction mixture was stirred at reflux (114–116° C.) until the area percent (AP) of benzophenone <9.0% by HPLC (22–29 h). The reaction mixture was cooled to 15–25° C. and water (35 mL) was added. After phase separation, the organic phase was concentrated to 50% (w/w) under reduced pressure at <40°. The concentrated solution was then cooled to 20° C., followed by addition of methanol (3 mL). The slurry was cooled to 10° C. and stirred for 30 min. The resultant slurry was filtered. The wet cake was washed with cold water/methanol (5:1 v/v, 2×20 mL), and dried under vacuum at 20° C. for 24 h to give N-(diphenylmethylene)glycine ethyl ester (2) as an off-white to yellow solid (5.5 g, 95% pure by HPLC, 65.6% isolated yield). $^1$H NMR (CDCl$_3$): δ 1.27 (t, J=7.25 Hz, 3H), 4.20 (s, 2H), 4.20 (q, J=7.07, 2H), 7.17–7.67 (m, 10H).

Preparation of Ethyl 2-(diphenylmethylene)amino-2-difluoromethyl-4-cyanobutanoate from N-(Diphenylmethylene) glycine Ethyl Ester

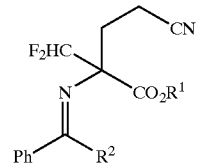

5

($R^1$=$CH_3CH_2$, $R^2$=Ph)

A 2 L reactor equipped with a thermocouple, reflux condenser and mechanical agitation, was charged with N-(diphenylmethylene)glycine ethyl ester (3, 100.0 g, 374.1 mmol, 1.0 eq). Acetonitrile (600 mL) was charged into the reactor and the mixture was agitated until the solid dissolved. K$_2$CO$_3$ (103.5 g, 748.2 mmol, 2.0 eq) was charged, followed by addition of 3-chloropropionitrile (30.7 mL, 392.8 mmol, 1.05 eq). The reaction was heated to 80° C. with vigorous agitation for 7–10 h. Conversion of compound of the formula 3 to compound of formula 4 was 95 AP. The reaction was cooled to ambient temperature, and the slurry was filtered and washed with 200 mL acetonitrile. The filtrate was transferred to a 2 L reactor equipped with a thermocouple and mechanical agitation. The filtrate was concentrated to a volume of ca. 300 mL. The reactor was charged with THF (400 mL), purged with N$_2$, and cooled to −20° C. NaOtBu (53.9 g, 561.1 mmol, 1.5 eq) was dissolved in THF (560 mL) and the mixture was cooled to −25° C. The cold NaOtBu solution was charged to the reactor over 3–4 min The reaction was agitated for a total of 7–10 min then chlorodifluoromethane (Freon-22®) was charged via a sparge tube at such a rate as to maintain the reaction temperature ≦−10° C. The reaction was judged complete with the end of the exotherm and the simultaneous change in color from dark red-black to light brown. The reaction mixture was allowed to warm to 20–25° C. then concentrated to a volume of ca. 500 mL. The reaction mixture was charged with EtOAc (600 mL) and H$_2$O (600 mL). The resulting mixture was agitated, and the phases were separated. The rich EtOAc solution was concentrated to a volume of ca. 300 mL. EtOH (400 mL) was charged and the mixture was concentrated again to a volume of ca. 300 mL. The solvent swap was repeated with an EtOH charge (400 mL), and the solution was concentrated to a final volume of ca. 500 mL. The rich EtOH solution was cooled to 0–5° C.

After a slurry started to form, the solution was agitated for 15 min. H$_2$O (156 mL) was charged at such a rate as to maintain the slurry temperature ≦5° C. After complete addition of H$_2$O, the slurry was agitated for 5–10 mins. The cold slurry was filtered and the cake was washed with −10° C. EtOH/H$_2$O (200 mL, 50:50). The product was dried under vacuum at ≦50° C. The yield of orange granular ethyl 2-(diphenylmethylene)amino-2-difluoromethyl-4-cyanobutyrate (5) was 113.4 g "as is", 69.9 M % corrected.

Ethyl 2-(diphenylmethylene)amino-4-cyanobutyrate (4)

$^1$H NMR (CDCl$_3$): 1.29 (t, 3H), 2.30 (m, 2H), 2.52 (m, 2H), 4.21 (m, 3H), 7.23–7.71 (m, 10H).

Ethyl 2-(diphenylmethylene)amino-2-difluoromethyl-4-cyanobutyrate (5)

$^1$H NMR (CDCl$_3$): 1.15 (t, 3H), 2.38 (m, 1H), 2.52 (m, 1H), 2.74 (m, 2H), 3.79 (m, 2H), 6.14 (t, 1H), 7.14–7.63 (m, 10H).

EXAMPLE 4

(Process A, Route II) Reduction of Ethyl 2-(diphenylmethylene)amino-2-difluoromethyl-4-cyanobutyrate (5) to 2-(Difluoromethyl)ornithine Ethyl Ester Dihydrochloride with 10% Pt-C

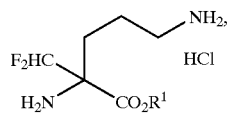

7

(R$^1$=CH$_3$CH$_2$)

To a 460 mL hastelloy bomb was added 10% Pt-C (2.2 g) and EtOH (30 mL). The contents were agitated and pressurized under hydrogen (95 psi) for 1 h. To the vessel was then added concentrated HCl (20.8 g, 4 eq) and compound of the formula 5 (20 g), as a solution in EtOH (170 mL). The contents were repressurized and agitated (500 rpm) until the substrate was gone (8–9 h). The reaction mix was then filtered over a Buchner funnel and washed w/2×20 mL EtOH. The resulting filtrate was refiltered over diatomaceous earth (Celite®) and the pad washed with 2×20 mL EtOH. The filtrate was then concentrated under vacuum at 40° C. while EtOH (310 mL) was added to compensate for volume loss. Distillation was continued until the final mass was ~80 g (25% w/w). MTBE (120 mL) was then added over 10 min at 40° C. to facilitate crystallization of the compound of formula 7. After cooling to room temperature, the slurry was agitated for one h, filtered over a Buchner funnel, and the cake washed with 2×20 mL MTBE. After being pulled dry, the crude weight was 11.65 g (76.2% yield).

$^1$H NMR (MeOD): δ 1.30 (t, J=7.2 Hz, 3H), 1.54–1.66 (m, 1H), 1.78–1.92 (m, 1H), 1.97–2.06 (m, 1H), 2.11–2.20 (m, 1H), 2.93 (t, J=7.2 Hz, 2H), 4.31–4.40 (m, 2H), 6.49 (dd, J$_1$=54.0 Hz, J$_2$=50.4 Hz, 1 Hz).

Calcd. for C$_8$H$_{18}$Cl$_2$F$_2$N$_2$O$_2$: C(33.94%), H(6.41%), Cl(25.04%), F(13.42%), N(9.89%), O(11.30%).

Found: C(32.57%), H(6.49%), Cl(26.15%), F(12.82%), N(9.90%), O(12.07%).

Alternative Reduction of Ethyl 2-(diphenylmethylene)amino-2-difluoromethyl-4-cyanobutyrate to Compound of Formula 7 using NaBH$_3$(OCOCF$_3$)

To a 50-ml, 3-neck, round bottomed flask equipped with stir bar and thermocouple was added NaBH$_4$ (0.52 g, 5 eq) and THF (15 mL). The flask was cooled to 10–20° C. and CF$_3$CO$_2$H (1.04 mL, 5 eq) is added as a solution in THF (5 mL) over 10 min. Compound of the formula 5 (R$^1$=CH$_3$CH$_2$, R$^2$=Ph) (1 g) was then added to the reaction mix as a solution in THF (5 mL) over 5 min and the water bath was removed. The reaction mix was agitated at room temperature until substrate conversion was complete (5 h). The reaction mix was then cooled to 0–5° C. in an ice water bath and cold water (40 mL) was added to quench any remaining hydride reagent. The product was extracted with MTBE (3×20 mL) and the combined organic layers agitated with 6 N HCl (1.4 mL, 3 eq). The product mix was concentrated under vacuum. Conversion to product was seen to be 54%, with the remainder being unidentified side products.

DFMO by Acid Hydrolysis

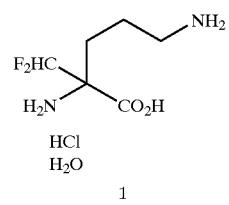

1

12 N HCl (141.3 mL, 1695.3 mmol, 16 eq) was added to compound of the formula 7 (30 g, 105.95 mmol, 1.0 eq), and stirred at 110° C. for 16–18 h. Then the reaction was concentrated to 2.0–2.5 mL/g, followed by addition of ethanol (6.0–7.5 mL/g). After refluxing for 30 min, and cooling to room temperature, triethylamine was added to bring the pH to 3.8–4.4 where upon a crystal slurry was formed. Crude compound of formula 1 (22.1 g) was isolated in 88.2% yield, after cooling to 0° C.

Crude compound of formula 1 (20.0 g) was dissolved in water (70 mL) and treated with charcoal (3.0 g) at 90° C. for 1 h. The charcoal was filtered off, and rinsed with 10 mL of water. Then ethanol (240 mL) was added to the filtrate. The resulting slurry was heated to 40° C. for 3 h and then cooled to 0° C. to give compound of formula 1 in 84.6% yield, and an overall yield of 74.6%.

DFMO by Basic Hydrolysis

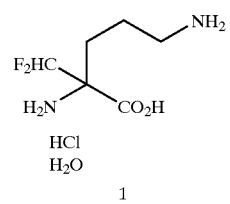

1

10 N sodium hydroxide (8.2 mL, 81.6 mmol, 3.3 eq) was added to a stirred solution of compound of formula 7 (7.0 g, 24.72 mmol, 1.0 eq) in water (18.2 mL). The mixture was heated at 100° C. for 3–5 h. The pH was then adjusted to 7 with 12 N HCl, followed by concentration to dryness. Additional 12 N HCl (8.6 mL/g) and ethanol (42 mL) was added. The slurry was then refluxed and cooled to 50–60°

C., and the inorganic salts were filtered off. Then the pH of the clear filtrate was adjusted to 3.8–4.4 with triethylamine, where upon a crystal slurry was formed. After refluxing for 15 min, followed by cooling to 0° C., crude compound of formula 1 (4.4 g) was isolated in 74% yield.

Crude crude compound of formula 1 (4 g) was dissolved in water (12 mL) and treated with charcoal (0.6 g) at 90° C. for 1 h. The charcoal was filtered off, and rinsed with 4 mL of water. Then ethanol (36 mL) was added to the filtrate. The resulting slurry was heated to 40° C. for 3 h and then cooled to 0° C. to give crude compound of formula 1 in 71.5% yield, and an overall yield of 52.7% (AP: 99.34).

EXAMPLE 5

(Process B) Reduction of Ethyl 2-Amino-2-difluoromethyl-4-cyanobutyrate to DFMO Lactam hydrochloride with Raney-Cobalt

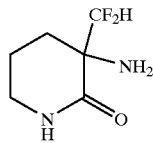

10

To a bomb equipped with plastic liner was added of ethyl 2-amino-2-difluoromethyl-4-cyanobutanoate (6, 0.5 g), Raney-Cobalt (5 g), and EtOH (15 mL). The contents were heated to 45° C., pressurized to 125 psi, and agitated with a stir bar until the reaction was complete (2–3 h). The reaction mix was then filtered over a Buchner funnel and the catalyst pad washed with EtOH. The filtrate was then concentrated on a rotary evaporator to ~1 g (40% w/w) and hexanes (5 mL) was added to facilitate agitation of the slurry of compound of formula 10. Filtration over a Buchner funnel, washing with hexanes, and drying yielded 0.14 g of compound of formula 10 (36.1%).

$^1$H NMR (MeOD): δ 1.60–1.72 (m, 1H), 1.76–1.94 (m, 2H), 1.98–2.10 (m, 1H), 3.11–3.32 (m, 2H), 5.88 (dd, $J_1$=57.6 Hz, $J_2$=57.6 Hz, 1H).

EXAMPLE 6

(Process D)

Preparation of Ethyl 2-Acetylamino-2-difluoromethyl-4-cyanobutanoate

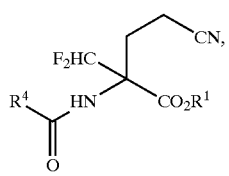

8

($R^1$=CH$_3$CH$_2$, $R^4$=CH$_3$)

To a 250 mL round bottom flask, was added 28.9 g of ethyl 2-amino-2-difluoromethyl-4-cyanobutanoate (6), 60 mL of dichloromethane, 0.71 g of DMAP, and 29.4 g of TEA at 0–5° C. Twenty-nine grams of acetic anhydride is then added dropwise through an addition funnel. The reaction mixture was heated to reflux (42° C.) for 5 h. After completion, the reaction mixture was charged with 90 mL of water, and adjusted to pH 7 by 2 N NaOH. The aqueous phase was extracted with dichloromethane (2×70 mL). The combined organic phases were dried with MgSO$_4$. After solvent removal under reduced pressure, a crude product was obtained (109.7% yield). The crude product can be purified by column chromatography.

$^1$H NMR (CDCl$_3$): δ 1.35 (t, J=7.0, 3H), 2.09 (s, 3H), 2.31–2.46 (m, 3H), 2.88–2.96 (m, 1H), 4.31–4.42 (m, 2H), 6.3 (dd, $J_1$=~55.5, $J_2$=~56.0, 1H), 6.55 (s, 1H).

Found: C(49.63%), H(5.51), N(11.11%), O(18.96%).

Calcd. for C$_{10}$H$_{14}$F$_2$N$_2$O$_3$: C(48.39%), H(5.68%), N(11.29%), O(19.34%).

Reduction of Ethyl 2-Acetylamino-2-difluoromethyl-4-cyanobutyrate to Ethyl 2-Acetylamino-2-difluoromethyl-5-aminobutyrate hydrochloride with 10% Pt-C

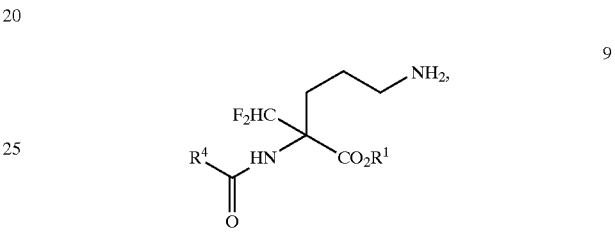

9

($R^1$=CH$_3$CH$_2$, $R^4$=CH$_3$)

To a 460 mL hastelloy bomb was added Pt-C (1.1 g) and MTBE (40 mL). The contents were agitated and pressurized under hydrogen (125 psi) for 1 h. To the vessel was then added concentrated HCl (11.2 g, 3 eq) and compound of the formula 8 (9.6 g) as a solution in MTBE (60 mL). The vessel and its contents were heated to 40° C., pressurized to 125 psi, and agitated for 5 h. The vessel was then cooled back to room temperature and agitated for 15 additional h. Following complete reaction, the reaction mixture was filtered over diatomaceous earth (Celite®) and the pad washed with MeOH. The filtrate was then concentrated. After being pulled dry, the crude product weight was 11.19 g (101.3% yield).

$^1$H NMR (MeOD): δ 1.20 (t, J=7.2 Hz, 3H), 1.67–1.76 (m, 2H), 1.90–2.06 (m, 2H), 1.94 (s, 3H), 2.86 (t, J=9.0 Hz, 2H), 4.16 (q, J=14.4 Hz, 2H), 6.24 (dd, $J_1$=57.6 Hz, $J_2$=54.0 Hz, 1H)

Calcd. for C$_{10}$H$_{19}$ClF$_2$N$_2$O$_3$: C(41.6%), H(6.63%), Cl(12.28%), F(13.16%), N(9.7%), O(16.62%).

Found: C(41.29%), H(6.48%), F(10.92%), N(8.83%)

DFMO from Ethyl 2-Acetylamino-2-difluoromethyl-4-cyanobutanoate by Acid Hydrolysis

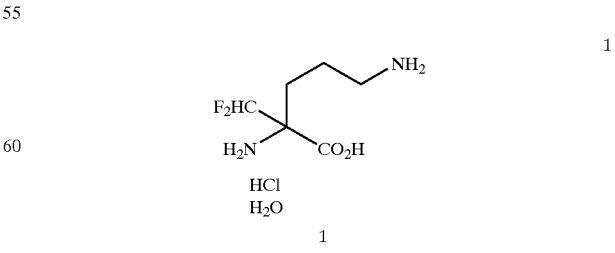

1

12N HCl (9.6 mL, 115 mmol, 16.6 eq) was added to compound of the formula 9 (2.0 g, 6.927 mmol, 1.0 eq), and stirred at 100° C. for 16 h. Then the reaction was concentrated to 2.0–2.5 mL/g, followed by addition of ethanol (6.0–7.5 mL/g). After refluxing for 30 min, and cooling to room temperature, triethylamine was added to bring the pH to 3.8–4.4 where upon a crystal slurry is formed. Crude compound of the formula 1 (1.02 g) was isolated in 59% yield, after cooling to 0° C.

Crude compound of the formula 1 (0.8 g) was dissolved in water (2.1 mL) and treated with charcoal (0.12 g) at 90° C. for 1 h. The charcoal was filtered off, and rinsed with 0.4 mL of water. Then ethanol (9.6 mL) was added to the filtrate. The resulting slurry was heated to 40° C. for 3 h and then cooled to 0° C. to give compound of the formula 1 in 65.3% yield, and an overall yield of 38.5% (AP: 100).

Definitions

The following terms shall have, for the purposes of this application, the respective meanings set forth below.

aryl shall mean a phenyl or substituted phenyl. Preferred phenyl substituents include $C_1$ to $C_6$ alkyl, $C_1$ to $C_6$ alkoxy and halogen.

Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A process for the preparation of a compound of the formula

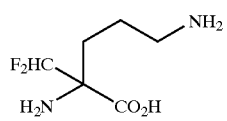

the process comprising:
providing an intermediate compound having fluorine and a nitrile moiety; and
selectively reducing said nitrile moiety to form an amine moiety,
wherein said intermediate compound is:

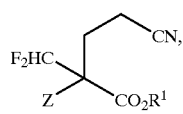

wherein $R^1$ is linear or branched $C_1$ to $C_4$ alkyl and Z is
(i) —$NH_2$ or
(ii) a moiety selected from the group consisting of

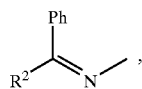

wherein $R^2$ is hydrogen, linear or branched $C_1$ to $C_4$ alkyl or aryl, and

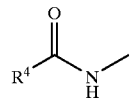

wherein $R^4$ is linear or branched $C_1$ to $C_4$ alkyl, alkoxy, or aryl.

2. The process of claim 1, wherein Z is

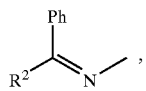

further comprising hydrolyzing the intermediate compound to produce a compound having one of the following formulas

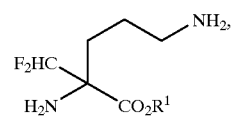

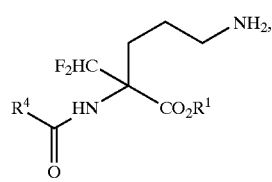

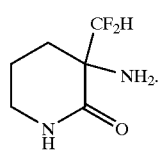

3. The process of claim 2 further comprising hydrolyzing the compound of formula 7, 9, or 10 to form the compound of formula 1.

4. The process of claim 1, wherein the intermediate compound is ethyl 2-benzylideneamino-2-difluoromethyl-4-cyanobutanote, ethyl 2-(diphenylmethylene)amino-2-difluoromethyl-4-cyanobutanoate, ethyl 2-amino-2-difluoromethyl-4-cyanobutanoate, ethyl 2-acetylamino-2-difluoromethyl-4-cyanobutanote, or a salt thereof.

5. A compound of the formula
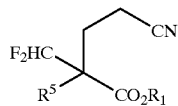
wherein $R^1$ is linear or branched $C_1$ to $C_4$ alkyl; and wherein $R^5$ is:
(a)
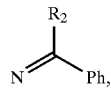
wherein $R^2$ is hydrogen, linear or branched $C_1$ to $C_4$ alkyl or aryl;
(b) $NH_2$; or
(c)
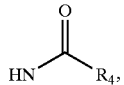
wherein $R^4$ is linear or branched $C_1$ to $C_4$ alkyl, alkoxy or aryl.
6. The compound of claim 5 wherein $R^1$ is selected from the group consisting of methyl, ethyl, and t-butyl.
* * * * *